US009795325B1

(12) United States Patent
Merzenich et al.

(10) Patent No.: US 9,795,325 B1
(45) Date of Patent: Oct. 24, 2017

(54) AUDITORY PERCEPTUAL SYSTEMS

(71) Applicant: POSIT SCIENCE CORPORATION, San Francisco, CA (US)

(72) Inventors: Michael M. Merzenich, San Francisco, CA (US); Wesley Marshall Jackson, Daly City, CA (US)

(73) Assignee: POSIT SCIENCE CORPORATION, San Francisco, CA (US)

( * ) Notice: Subject to any disclaimer, the term of this patent is extended or adjusted under 35 U.S.C. 154(b) by 473 days.

(21) Appl. No.: 14/211,164

(22) Filed: Mar. 14, 2014

Related U.S. Application Data

(60) Provisional application No. 61/782,571, filed on Mar. 14, 2013.

(51) Int. Cl.
A61B 5/00 (2006.01)
A61B 5/12 (2006.01)
H04R 25/00 (2006.01)
G09B 19/04 (2006.01)

(52) U.S. Cl.
CPC .............. A61B 5/123 (2013.01); G09B 19/04 (2013.01); H04R 25/30 (2013.01)

(58) Field of Classification Search
CPC ........... A61B 5/12–5/123; A61B 5/742; A61B 5/7435; A61B 5/748; H04R 25/30; H04R 25/70
USPC ....................................................... 600/559
See application file for complete search history.

(56) References Cited

U.S. PATENT DOCUMENTS

2003/0078515 A1\* 4/2003 Menzel ................ A61B 5/0002 600/559
2014/0257131 A1\* 9/2014 Polley .................... A61B 5/123 600/559
2015/0025413 A1\* 1/2015 Shennib ................. A61B 5/123 600/559

FOREIGN PATENT DOCUMENTS

CH WO 2014090299 A1 \* 6/2014 ........... A61B 5/7221

\* cited by examiner

Primary Examiner — Daniel Cerioni
(74) Attorney, Agent, or Firm — Eric W. Cernyar; James W. Huffman

(57) ABSTRACT

A new hearing profile assessment plays each of a plurality of frequency tones multiple times at a plurality of loudness levels. For each frequency, the patient indicates which tones that they can hear, establishing minimum-amplitude thresholds for each frequency. The assessment adapts loudness levels until the patient indicates consistent minimum-amplitude thresholds for each frequency. Also, a new system for training the hearing of a subject is disclosed. The system instructs the subject to vocalize various sound items and remember the sounds that they vocalize. The system plays either recorded samples of the subject's own voice, or comparison samples of a synthesized voice or other's vocalizations of the same sound items. The system prompts the subject to compare the played samples with the sounds they remembered vocalizing. The system uses the feedback to adjust sound processing parameters for a hearing aid, cochlear implant, sound output devices, or a training program.

11 Claims, 13 Drawing Sheets

AUDITORY PERCEPTUAL SYSTEMS

CROSS REFERENCE TO RELATED APPLICATION(S)

This application claims the benefit of U.S. Provisional Application No. 61/782,571, filed Mar. 14, 2013, for a "Novel Strategy to Accelerate Recovery of Speech Understanding in Individuals with Cochlear Implants or Hearing Aids," which is herein incorporated by reference for all purposes.

FIELD OF THE INVENTION

This invention relates in general to hearing health and in particular, to auditory perceptual training to correct hearing loss.

BACKGROUND OF THE INVENTION

Hearing Loss.

Hearing loss effects nearly 40 million Americans, but many individuals suffering from hearing loss or other hearing-related disorders do not seek clinical help because of stigma, financial constraints or other obstacles, and many people are unaware of their hearing impairment.

Even people fitted with hearing aids show limited success because the devices do not account for the detrimental neural changes induced by hearing loss that prevent the user from maximally exploiting low-level speech cues, such as subtle changes in frequency and timing.

Impaired hearing desensitizes the cortex to hearing-loss frequencies and degrades its ability to distinguish auditory input. These cognitive deficits disrupt higher-level auditory processing like phoneme discrimination, ultimately impairing the hearing-impaired individual's ability to engage in and remember conversations.

Hearing aids do not correct this pathological neural function because the cortex must be trained to properly discriminate and utilize the frequencies amplified by the aid along with other auditory information lost from degraded input.

Auditory perceptual training can reverse the pathological plasticity associated with hearing loss by training the individual to make the necessary temporal, intensity and frequency discriminations required for healthy hearing abilities. As these discriminations are fundamental to phoneme processing, such training can improve speech perception. In fact, phoneme discrimination training has been shown to improve speech perception in hearing-impaired individuals beyond the benefit of a hearing-aid alone. Although previous art has shown that auditory perceptual training can improve speech perception in hearing-impaired individuals, such training has not been tailored to individuals' personal hearing needs.

There is a need for individually-tailored auditory perceptual training. There is a concomitant need for practical automated systems and methods for tailoring auditory perceptual training to an individual.

Audiometry.

There are many methods of audiometry for diagnosing hearing loss. But current clinical audiometric methods are not able to be implemented on personal computers operable by a layperson; i.e., the sufferer of hearing loss. Current clinical audiometric devices require a trained audiologist to operate and interpret the test results in the form of an audiogram. Worse, apparently similar audiograms may permit multiple interpretations because of technical variations in audiometric methods and test subject idiosyncrasies. These and other complications must be overcome to make audiometric methods simple enough for the sufferer to use themselves, and accessible enough to be used on their own device (such as a personal computer via the internet).

There are additional obstacles to developing a layperson-operable audiometric device. The sound output by sound cards and headphones varies from one device to another. Ensuring accurate sound pressure levels across the range of tested frequencies requires calibration of the sound output to compensate for distinct frequency responses of the computer's sound card and the headphones used during the test. Also, sine tones commonly presented in audiometry can produce harmonic distortion when presented at intense levels. Additionally, personal computers produce noise that may interfere with the user's performance.

Also, current audiometric methods focus only on quantifying hearing thresholds. We are aware of no prior art audiometers that inform perceptual training software as to what kinds of sound discriminations would be most useful for the user.

SUMMARY

A new audiometric assessment method is provided. In one embodiment, the method involves presenting a game that plays a plurality of tones spanning a plurality of frequencies, with each tone played at a plurality of loudness levels distributed across discrete decibel increments. A player indicates which of the tones, if any, they can hear. For each frequency, the assessment adapts the loudness levels of the tones and replays the tones until the player identifies a consistent minimum-amplitude threshold. The player only compares tones of the same frequency, and is assessed for a new frequency once a consistent hearing threshold has been established.

The game challenges the user to indicate as rapidly as possible whether they can hear the tones. The game provides sensory feedback on the accuracy and speed of the user's response.

In an exemplary embodiment, the game displays a plurality of selectable visual objects, each associated with one of the tones. The player is challenged to hover a pointer over the objects to play the tones and to select the objects if they are able to hear the tones.

Advantageously, the audiometer quickly, accurately and consistently derives the prominent regions of hearing impairment.

A new audio perception training method and system is also provided. The system instructs the subject to vocalize sound items and remember the sound items that they vocalize. In one embodiment, the system records samples of the subject's voice and plays the recorded samples back. In another embodiment, the system plays samples of synthesized speech or other persons' voices. The system then prompts the subject to compare the played sample with the sound they remembered vocalizing and provide feedback on the comparison. The system then adjusts sound processing parameters on the basis of the subject's feedback. In one embodiment, the sound processing parameters calibrate a hearing aid or cochlear implant worn by the patient. In another embodiment, the sound processing parameters calibrate the output of a sound card, speaker or other sound output device.

The system repeatedly procures sound item samples from the subject and feedback from the subject comparing played samples with the sound or sounds they remembered vocalizing. The system progressively adjusts the sound processing parameters until the subject indicates that they are satisfied that the played samples sound similar to what they remembered vocalizing, or a threshold number of adjustments have been made, or an evaluation of the subject's feedback indicates a marginal benefit to further adjustments.

In another embodiment, an audiometric or cognitive training program selects optimal stimuli—such as stimuli using frequencies to which the subject is least sensitive—to use in subsequent games that are a function of the results obtained from the assessment. Such training, coupled with a hearing aid or cochlear implant, focuses on regions of newly-acquired hearing. The cortical regions corresponding to one's hearing loss are largely inactive and poorly tuned despite amplified input from the device. The auditory perceptual training allows cortical response to the amplified input to be normalized. To render the training even more effective, the training program uses an audiometer or other method of hearing threshold estimation to ensure optimal stimuli are selected for training.

Other features and advantages of the present invention will become apparent upon study of the remaining portions of the specification and drawings.

DETAILED DESCRIPTION

Various embodiments of the present invention use a computer system and a computer network for executing one or more cognitive training computer programs, where "cognition" refers to the speed, accuracy and reliability of processing of information, including filtering, recall, and manipulation of information, and attention and/or working memory.

A typical computer system (not shown) for use with the present invention will contain a computer, having a CPU, memory, hard disk, and various input and output devices. A display device, such as a monitor or digital display, provides visual prompting and feedback to the subject during execution of the computer program. Speakers or a pair of headphones or ear buds provide auditory prompting and feedback to the subject. A printer may be connected to the computer to enable a subject can print out reports associated with the computer program. Input devices such as a keyboard, mouse, trackpad, touch screen, microphone, camera, or other sensor receive input from the subject. A number of different computer platforms are applicable to the present invention, including but not limited to embodiments that execute on IBM compatible computers, Macintosh computers, phones, tablets, set top boxes, PDA's, and gaming consoles.

A computer network (not shown) for use with the present invention contains multiple computers similar to that described above connected to a server. The connection between the computers and the server can be made via a local area network (LAN), a wide area network (WAN), or via modem connections, directly or through the Internet. The computer network allows information such as test scores, game statistics, and other subject information to flow from a subject's computer to a server. An administrator can review the information and can then download configuration and control information pertaining to a particular subject to the subject's computer.

I. General Characteristics

Figure 1:
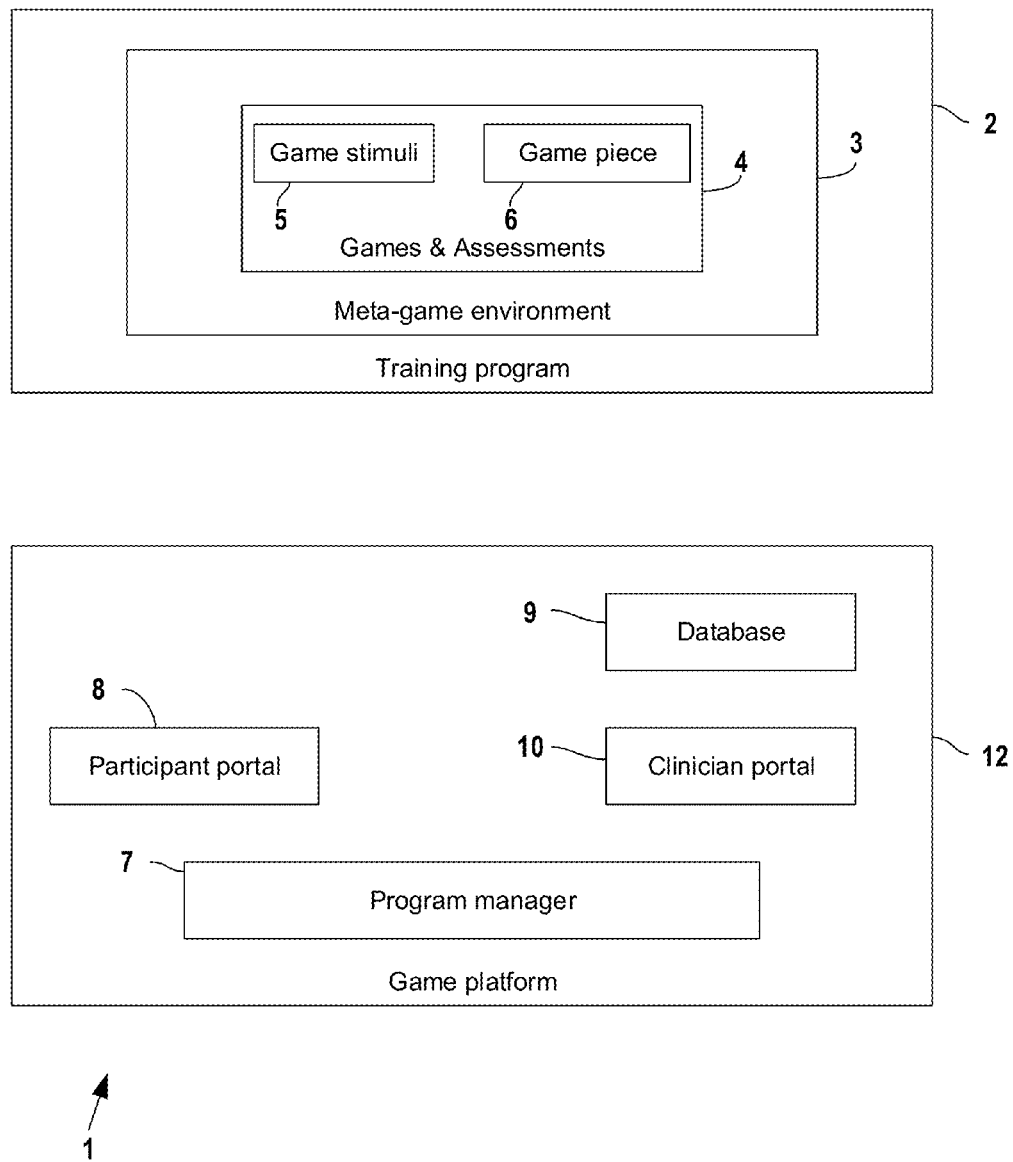
FIG. 1 is a block diagram of one embodiment of a multi-faceted, web-deliverable, and game-based cognitive training system.

FIG. 1 is a block diagram of one embodiment of a multi-faceted, web-deliverable, browser-playable and game-based neurological training system 1 configured to treat a cognitive deficit. The neurological training system 1 is described in more detail in U.S. patent application Ser. No. 14/201,666 filed Mar. 7, 2014, entitled "Neuroplasticity Games," which is herein incorporated by reference for all purposes.

The neurological training system 1 comprises a game platform 12 and training program 2. The game platform 12 controls exercise delivery and records all data on game play and performance progressions for exercise suites playable on Internet-connected computers and pads. It comprises a program manager 3, participant portal 8, clinician portal 10, and database 9. The program manager 3—also referred to herein as a game manager—is configured to administer the training program 2, manipulate a plurality of game stimuli 5, and receive input from at least one game piece 4.

The training program 2 comprises a plurality of games or exercises 4. In some embodiments, the training program 2 targets a plurality of cognitive domains and sensory modalities, from foundational ones like processing speed to more complex ones like social cognition. Each training program 2 is customized and configured to address cognitive deficits that are associated with a neurological condition, such as hearing loss, addiction, depression, ADHD, or ASD, and its co-morbidities.

In most embodiments, the game stimuli comprise images displayed on a display device such as a computer monitor or digital screen and/or sounds played through a speaker, ear buds or other auditory equipment. In other embodiments, the game stimuli comprise smells, tastes, or tactile (e.g., haptic) stimulation. The training program's stimulus set is designed to span the relevant dimensions of real-world stimuli to ensure that learning is never stimulus specific.

Early in training, the games use highly salient, emphasized (e.g., high contrast, temporally deliberate) stimuli to drive strongly synchronized brain responses requisite for rapidly driving brain changes in a corrective way. The games then progressively move to more ecologically-relevant and valid stimuli (e.g., real speech, complex realistic social stimuli with people showing emotions in context, social scenes, social interactions) to ensure generalization to real-world situations.

The game piece 6 comprises a keyboard, computer mouse, track pad, touch screen, camera, remote sensing device (e.g., Microsoft Kinect®), microphone, or other input device.

The training program 2 provides the games through a portal 8 that is designed to be played in a social network environment, at a treatment center, or during a treatment class. In one embodiment, the training program 2 is designed to be platform-independent so that it can be delivered over the Web via any Internet-connected computer. In another embodiment, the training program 2 is provided through a hand-held computer (iPhone/Android phone/iPad/Android tablet/Amazon Fire) application.

The participant portal 8 provides access to game participants. Practically any patient on any computer located anywhere in the world can work on these programs as frequently as their time and schedule permit, under the supervision of a clinician who can (hypothetically) also be located anywhere. To use the program, a participant opens a standard web browser on a broadband connected computer and goes to a program web site. The participant then logs into the program using a screen name that contains no personally identifiable information.

In one embodiment, the portal 8 introduces the participant to a "meta-game wrapper" such as an image and map of a virtual social city that allows participants to visit locations, access games, view progress and results, and make or communicate with friends. The meta-game wrapper is characterized by simplicity, appealing graphics, a sense of control, and constant game rewards.

The program manager 7 administers a schedule that ensures that a participant progresses through the games 4 in a defined order, generally moving from more simple (early sensory processing) games 4 to more complex (multimodal, working memory, memory span) games 4 over the course of a multi-week experience. At any point in time, the participant has access to a subset (for example, eight) of the games 4, and is challenged to perform at least a certain number (for example, six) of the games 4 per day. Each game 4 has specific criteria for completion or plateaued performance. After those criteria are met, the game 4 is removed from the active set and the next game 4 added to it. This mechanism ensures ongoing novelty and engagement for the participant, while ensuring that the participant progresses smoothly through the complete set over the program use period.

Within each game 4, a performance threshold, determined by an appropriate up-down procedure or a Zest algorithm, is derived for each block completed. The performance threshold provides performance and improvement data on the individual games. Game-based assessments, which are designated blocks with medium difficulty of the specific games 4, are performed at various time points in the intervention to check progress.

The games 4 in the training program 2 are designed with a different objective than conventional games. Conventional games start at a fixed baseline and progress in a single direction, getting more difficult until the participant is unable to go any further, at which point the game typically terminates. Conventional multilevel games also require completion of one level to progress to the next, more difficult, level, terminating mid-level if the participant is unable to complete a given level.

The games 4 of the training program 2, by contrast, are adaptive and threshold-based. Learning rules are relaxed in initial training to assure near-errorless learning. Error rates are slowly increased to achieve challenge conditions known to be optimal for normal individuals by the end of the training epoch. Likewise, rewards or incentives for performance gains are initially amplified, in comparison with those applied for training in other patient populations. The games 4 increase in difficulty when the participant exceeds a threshold of success, and they decrease in difficulty when the participant's performance drops below another threshold. Many of the games 4 enable a participant to "unlock" a new level merely by beating the participant's previous best score. By measuring success in metrics of personal improvement rather than fixed performance requirements, both participants with relatively high cognitive abilities and participants with relatively significant cognitive deficits can progress through the entire training program 2.

After logging in, a game-like experience begins in which the participant is encouraged to earn points and in-game rewards to further advance in each game 4. To do so, the participant selects one of the games 4 scheduled for the day, and performs that game for 5-10 minutes. The game 4 itself contains the core science stimuli and task built into a game-like experience. Performing the game 4 resembles practice on a skill akin to learning to play an instrument or learning to ride a bicycle.

Participants perform tens to hundreds of trials over the course of the ten-minute session. Each trial provides auditory and visual feedback and rewards to indicate if the trial was performed correctly or incorrectly. After each trial, the difficulty of the next trial is updated to ensure that within each session, the participant gets ~85% of trials correct. Maintaining a relatively high level of success helps prevent frustration and minimizes the possibility of potential dropout from the program. Summary screens including game metrics (points, levels) and game metrics (usage, progress) are shown to the participant at the end of each session.

To progress through a game 4, the participant performs increasingly difficult discrimination, recognition, memorization or sequencing tasks under conditions of assured focused attention. Each game 4 employs adaptive tracking methods to continuously adjust one or two adaptive dimensions of the task to the sensory and cognitive capabilities of the participant. This process is based on a statistically optimal Bayesian approach that allows the games 4 to rapidly adjust to an individual's performance level, and maintain the difficulty of the stimulus sets at an optimal level for driving most-efficient learning.

This continuously-adjusted adaptivity operates from trial to trial, to sustain an individual's performance success at a challenging (80-90%), since subject is not correct all the time, yet engaging and rewarding (since subject is correct most of the time) level of performance success. This continuously-adjusted adaptivity is also adjusted across sessions to ensure that the games 4 become more challenging at exactly the appropriate rate for a specific individual's rate of learning. This adaptivity also allows the game 4 to adapt to an individual's variable performance across days depending on their overall mood, attention, and health.

By this strategy, training is individualized. A trainee rapidly progresses across training landscapes for which impairments are mild or insignificant but must work hard to improve domains of substantial impairment—always working on the edge of their achievable performance abilities to drive positive, corrective changes at an optimized day-by-day rate, to address the specific neurological problems that most specifically frustrate their higher functioning.

If a game 4 is used as a training module, it is presented as stages that last about ten minutes. During those ten minutes, the participant plays the stage two times: first to set a baseline, and second to beat or match that baseline. This repetition is intentional, because the targeted strengthening of certain neural pathways achieved in the games requires repeated activation of those neural pathways. Stages generally have one level (block of trials intended to be played straight through), but they can have more.

The program manager 7 delivers all patient performance data in encrypted forms to a cloud-located database 9, which are provided, with appropriate informed consents, to one or more treatment program professionals, who access the relevant patient data through a clinician portal 10 in order to supervise patient treatment and assure enrollment, compliance, and monitored and guided patient progress.

Every aspect of a patient's compliance and progress is recorded in training and can be provided via the cloud-based database 9 (with appropriate permissions) to supervising training monitors or professionals. No personally identifiable information (including Internet protocol addresses) is stored on the server. The server makes the data available for review by the clinician(s) supervising patient care, the site trainer, site coordinator, and site investigator through a secure web portal 10, which requires a complex password to secure the identification of these individuals. Only data from participants in a particular clinic can be viewed by that clinic's staff. The site trainer, in particular, uses the secure web portal 10 to regularly check on usage and progress of each active participant to customize their weekly phone/in-person/social network discussions to provide helpful guidance and coaching.

II. Assessments

Each training program 2 utilizes assessments to personalize the types of games, types of stimuli, and levels of difficulty to the participant. Each game 4 can be used as an assessment or a training module. If a game 4 is used as an assessment, it is played once through before the participant advances to the next game.

Playing an assessment typically lasts five or fewer minutes. Assessments are used sparingly to avoid inducing learning/practice effects. In assessments, progressive variables that change an exercise's difficulty may be removed to provide a static reading of performance. Visual and/or auditory feedback and rewards may also be removed to reduce effects related to trial-by-trial learning or motivation.

Assessments are embedded in the training program 2 in form of surveys and exercises of varying similarity to those selected for training. Assessments are placed before and after training and often during checkpoints within training. Checkpoints generally occur every 10 to 14 days of training and can be spaced further apart for longer training programs.

The training program 2 calibrates the games 4 based on pre-training assessment results to select games 4 and certain stages or levels within the games to present as part of the training program. The assessment-based calibration means adjusting the type and salience of stimuli. It some embodiments, the calibration also means adjusting the proportion of training exercises related to each cognitive domain (e.g., processing speed, attention, theory of mind, impulse control). Calibration is also used to adjust parameters within an exercise like the start point of the progressive variable or the number of trials in a block. Such parameters tend to be calibrated for adults with moderately high cognitive abilities. Young children and individuals suffering from cognitive impairments often require specialized settings.

1. Hearing Profile Assessment

Figure 2:
FIG. 2 illustrates a screenshot of one embodiment of an auditory assessment called "Hearing Profile."
Figure 3:
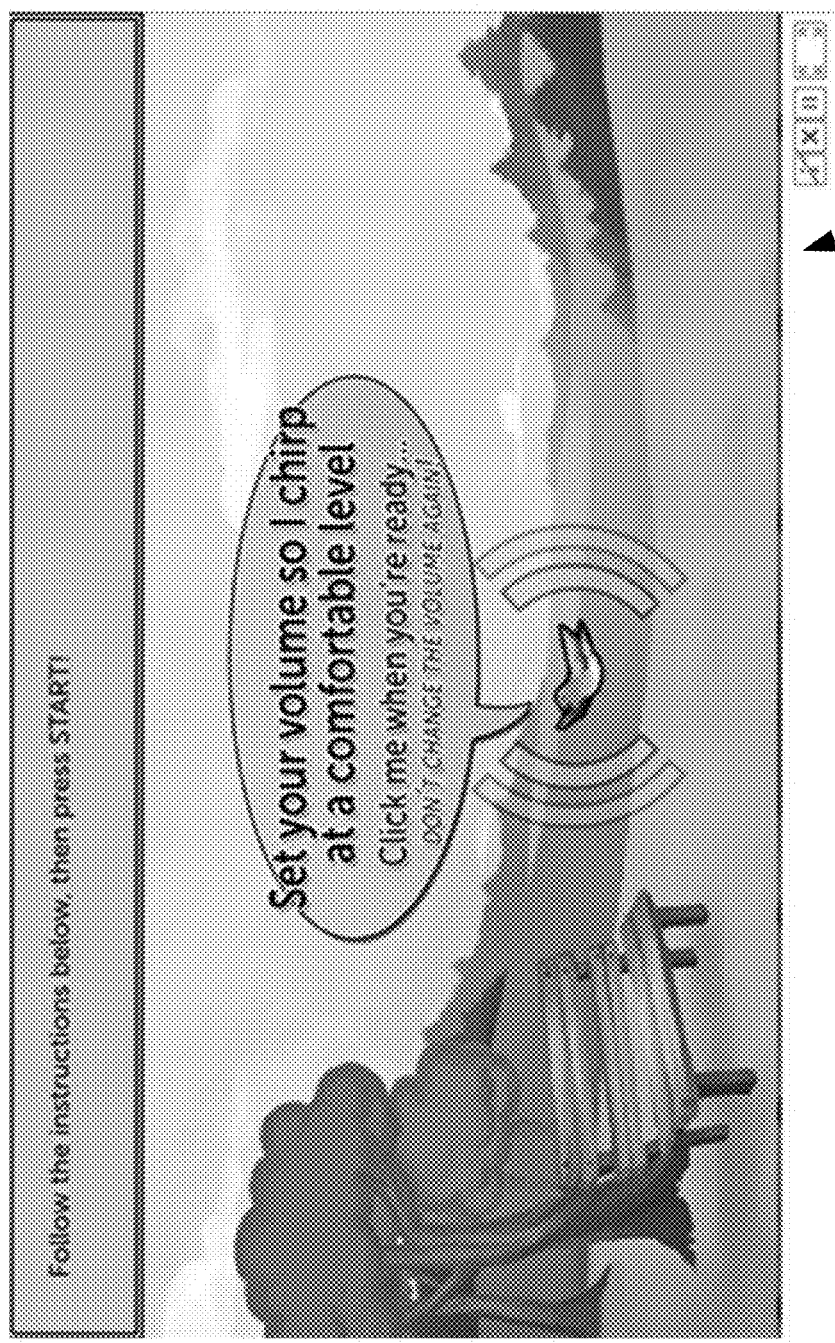
FIG. 3 illustrates another screenshot of the game illustrated in the previous figure.
Figure 4:
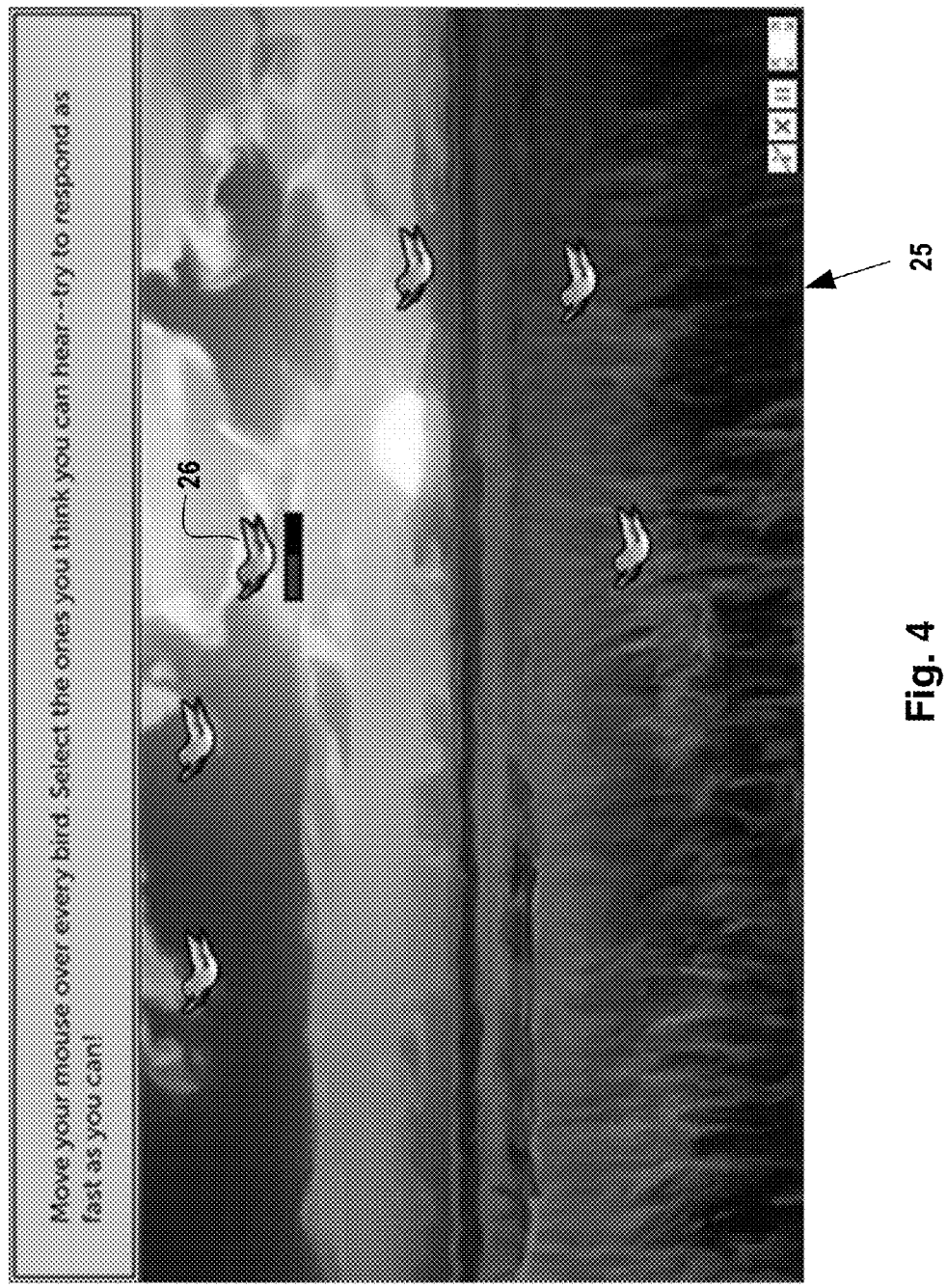
FIG. 4 illustrates another screenshot of the game illustrated in the previous figure.

FIGS. 2-4 illustrate screenshots 20, 22 and 24 of one embodiment of a hearing profile assessment that measures a participant's hearing loss. Hearing thresholds are obtained from 0.25-16 kHz, spanning the speech frequency range. Hearing thresholds for each frequency are obtained independently by finding the quietest volume level the frequency can be played at that the participant consistently judges to be audible. The hearing profile assessment is referred to herein as the multiple-interval staircase (MIS) assessment.

In FIG. 2, the assessment prompts the participant to maintain a consistent, quiet and controlled environment each time they take the hearing test to ensure conditions are comparable across tests. In FIG. 3, the assessment prompts the participant to calibrate their computer volume to a comfortable level to ensure enough test sounds will be audible yet not painful. In FIG. 4, the assessment presents images of multiple birds 26 on a screen. Each bird plays the same test frequency at different controlled loudness levels. The assessment instructs the participant to hover the mouse over each bird 26 and click it if they can hear it. If the participant hovers their cursor for too long over any single bird 26, the bird disappears and that decibel level for that frequency is considered to be inaudible. This process is repeated at quieter loudness levels until the participant consistently chooses the same loudness (decibel) level as the quietest bird they indicated as audible. This maximizes response consistency and minimizes the influence of uncontrolled environmental sounds.

Figure 5:
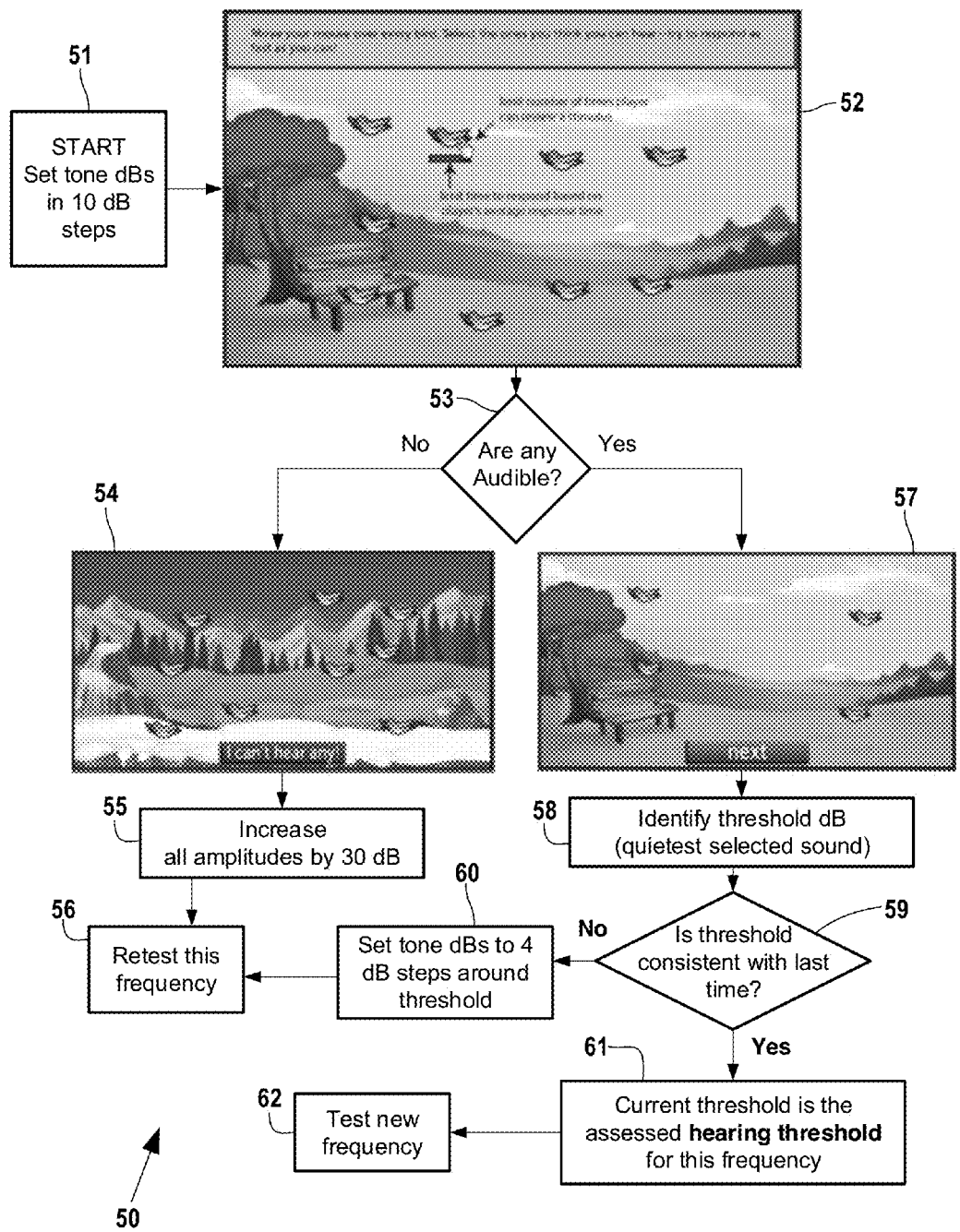
FIG. 5 is a functional block diagram of one embodiment of the auditory assessment of FIG. 2.

FIG. 5 is a functional block diagram of one embodiment of the MIS audiometry exercise and assessment 50. In block 51, the assessment 50 plays each of a plurality of tones or sound samples multiple times at a plurality of loudness levels, such as 10 dB loudness increments. Within block 51, each tone or sound sample is presented at a common frequency. Only the loudness level differs.

Block 52 illustrates a screenshot showing how the assessment 50 is, in this exemplary embodiment, embedded in a game that displays a plurality of visual objects over a scenic background. In this particular example, nine birds are shown, and each bird represents a different loudness level or a silent foil. As shown in block 52, the assessment 50 challenges the participant to move a mouse pointer over every bird and select the ones the participant can hear. The assessment 50 also challenges the participant to respond as fast as possible, illustrating a time bar that gives the participant a limited amount of time to select the bird. The assessment 50 limits the number of times a participant can hover the pointer over a bird to listen to the stimulus associated with that bird.

After detecting—based on a combination of mouse movements and possible mouse selections—that the user is done listening to all, or at least a sufficient number, of the tones, then flow proceeds to block 53. If the user indicated that any of the tones were audible, and the user's cumulative selections do not suggest an inordinate amount of error exhibited by foil selection or a distribution of selections that are not sufficiently positively correlated with loudness, then flow proceeds to block 57. If the user did not indicate that any of the tones were audible, then flow proceeds to blocks 54, 55, and 56. If the user's cumulative selections suggest an inordinate amount of error, then the assessment 50 repeats block 52 using the same loudness levels or the same median loudness level but with a greater distribution of loudness levels. Alternatively, the assessment 50 terminates.

Block 54 illustrates a scenic screenshot of birds flying in darkness, symbolizing the participant's inability to hear. After displaying this screenshot, the assessment 50 in block 55 increases the amplitude of each tone or sound sample by 30 dB and, in block 56, retests the tones or sound samples at the same frequency most recently tested.

Block 57, by contrast, illustrates a scenic screenshot of birds flying in daylight, symbolizing the participant's ability to hear. In block 58, the assessment 50 identifies the threshold loudness level, which is either the quietest selected loudness level or a statistical loudness level conservatively representative of the lower threshold of the participant's hearing.

Flow proceeds to block 59. If the last time the assessment 51 performed the actions illustrated with respect to block 52 was with the same frequency, and the identified threshold loudness level is consistent with—that is, either the same as or within a range of—the last identified threshold loudness level for that same frequency, then flow proceeds to block 61. Otherwise, flow proceeds to blocks 60 and 56, and the assessment 50 tests the same frequency again, but using loudness levels that are distributed more narrowly (e.g., 4 dB increments) around the identified threshold loudness level.

Once a consistent threshold loudness level is determined, then in block 61 the detected threshold loudness level is treated as the assessed threshold loudness level for that frequency. Flow proceeds to block 62, in which the assessment 50 tests the participant at a new frequency, repeating the actions illustrated at blocks 51 and 52. In this manner, the assessment 50 adapts the loudness levels of each frequency tone until a consistent minimum-amplitude threshold is identified.

Once the assessment 50 is completed, the training program 2 selects stimuli to use in a plurality of neuroplasticity games 4 that are a function of the results obtained from the audiometric exercise. Some of the neuroplasticity games 4 are auditory perceptual training games that use game stimuli comprising auditory signals.

2. Tinnitus Assessment

Figure 6:
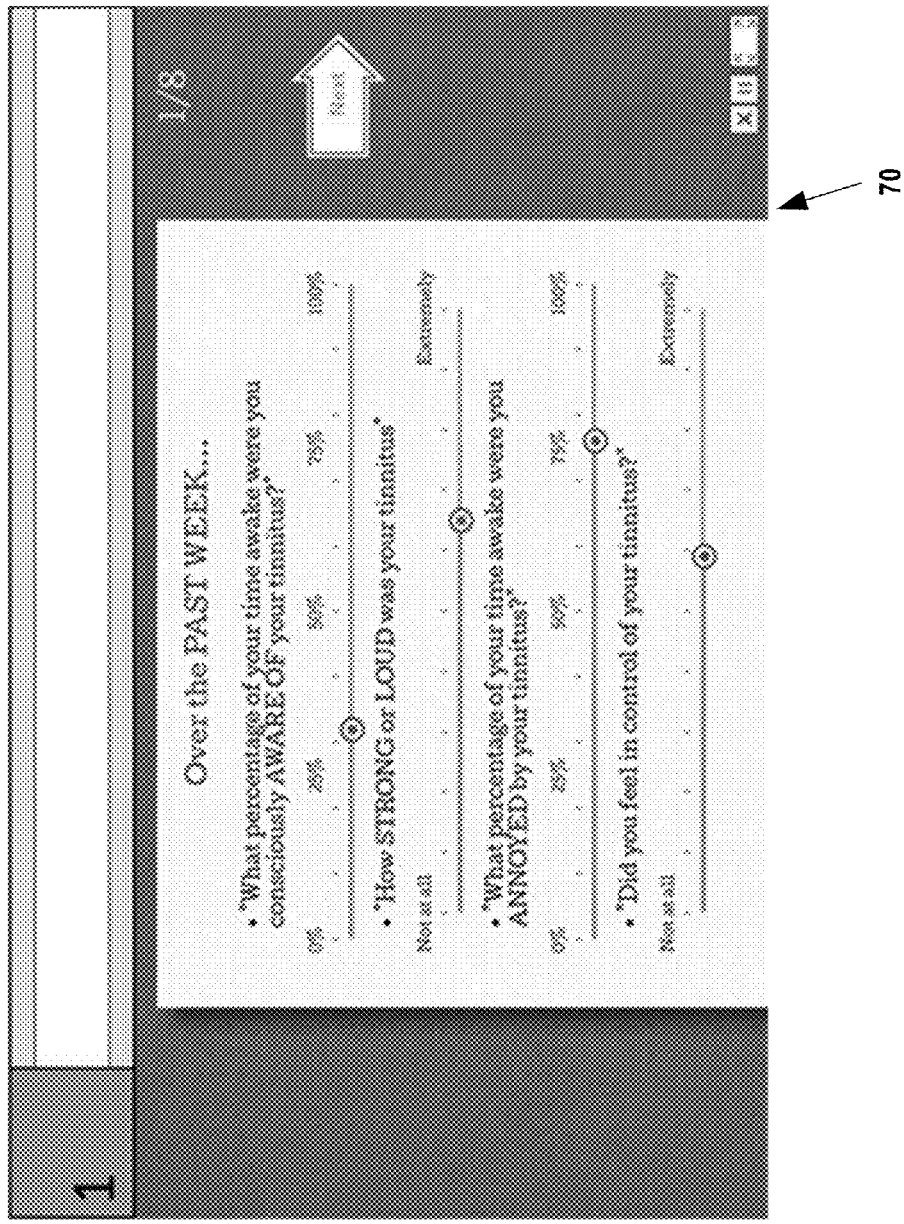
FIG. 6 is a screenshot of one embodiment of an online Tinnitus assessment.
Figure 7:
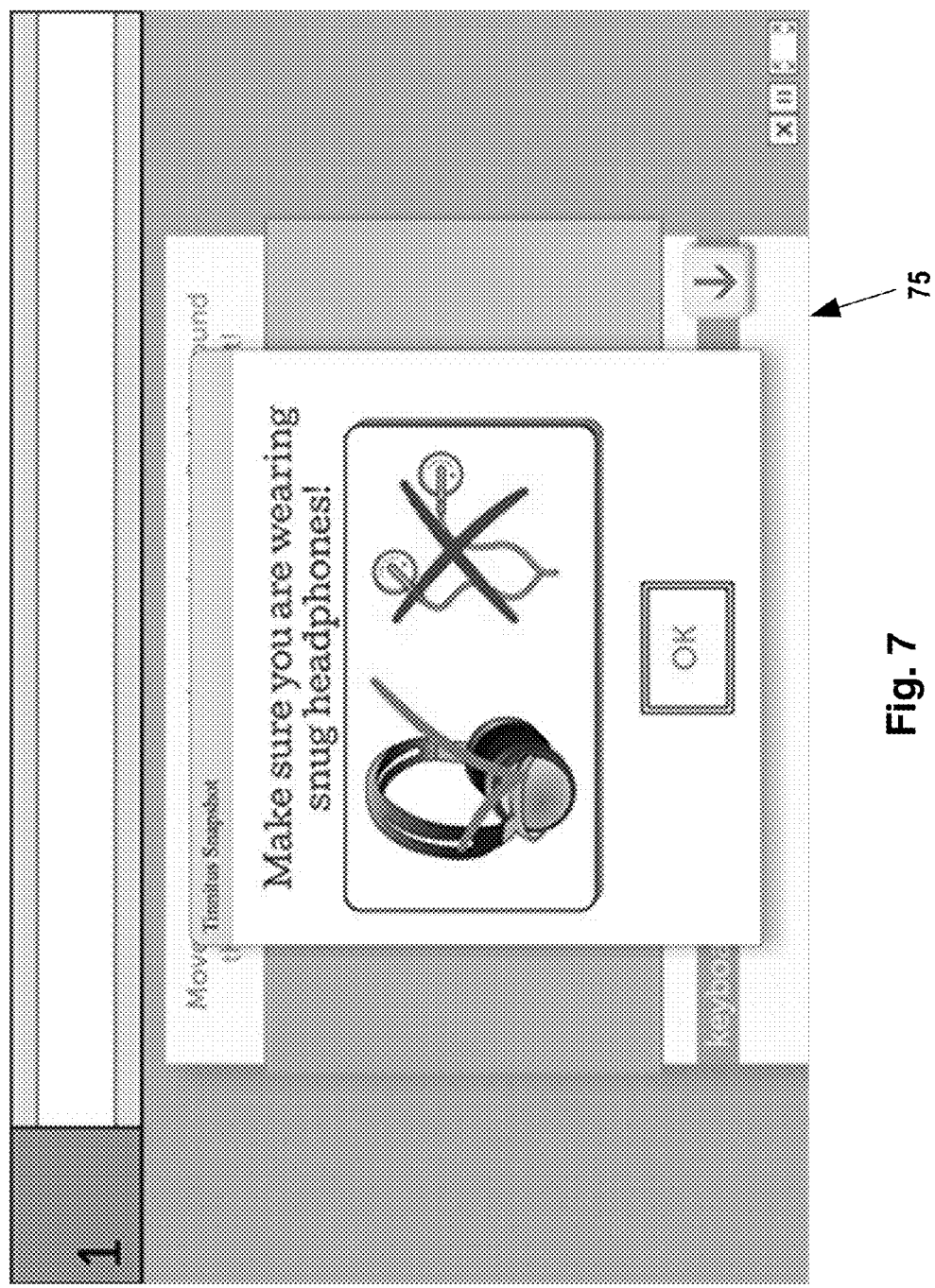
FIG. 7 illustrates another screenshot of the game illustrated in the previous figure.
Figure 8:
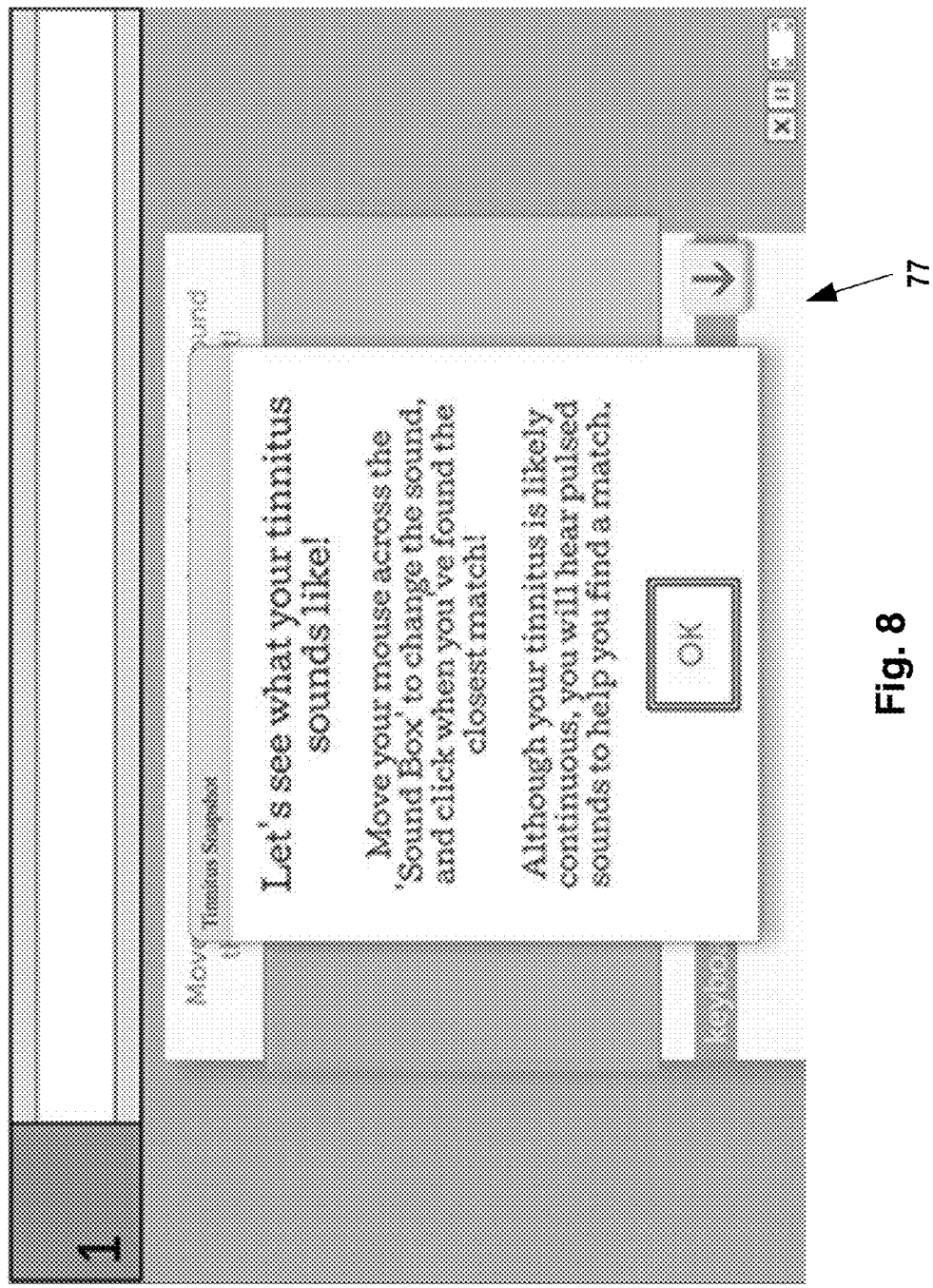
FIG. 8 illustrates another screenshot of the game illustrated in the previous figure.
Figure 9:
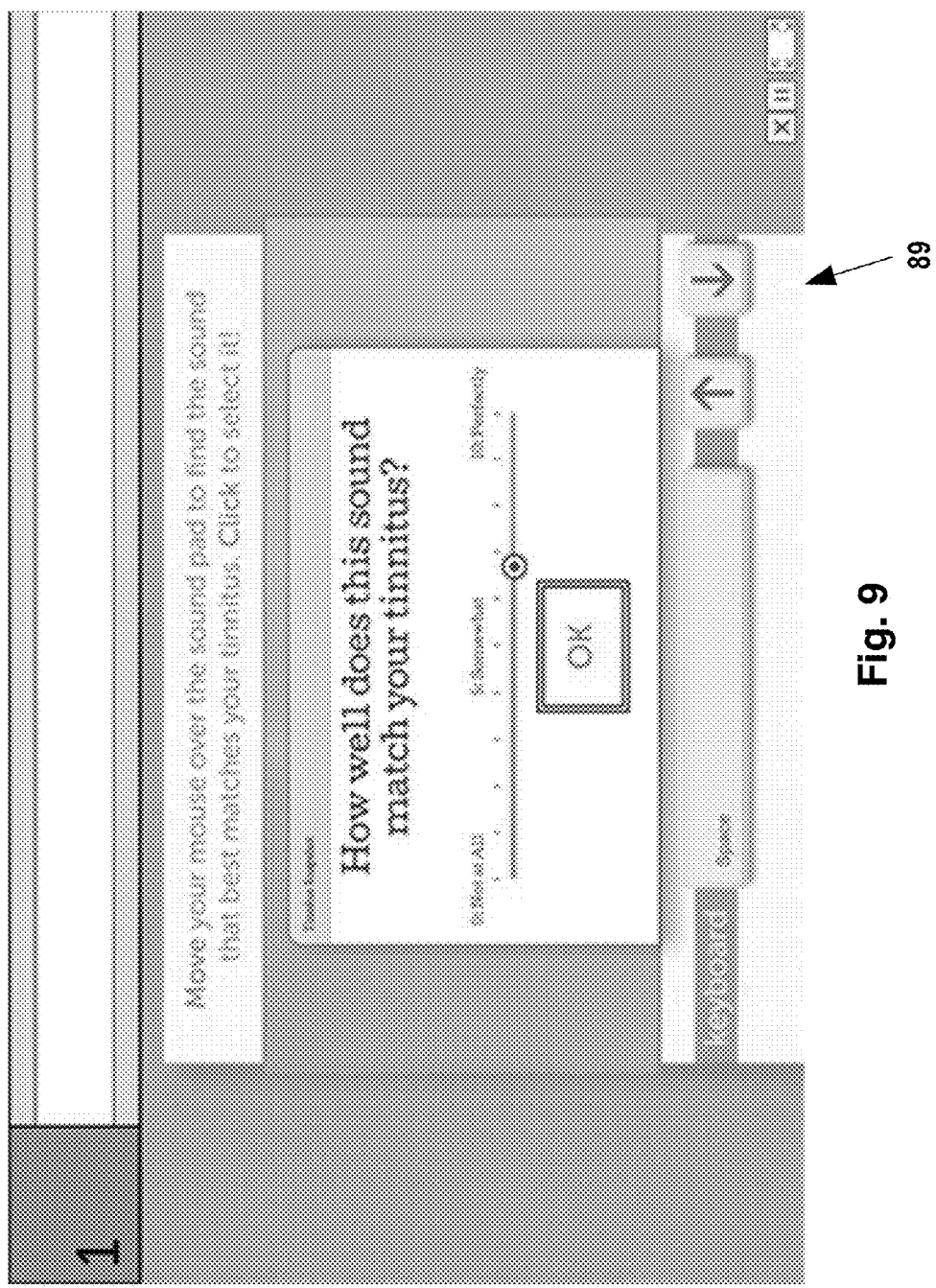
FIG. 9 illustrates another screenshot of the game illustrated in the previous figure.
Figure 10:
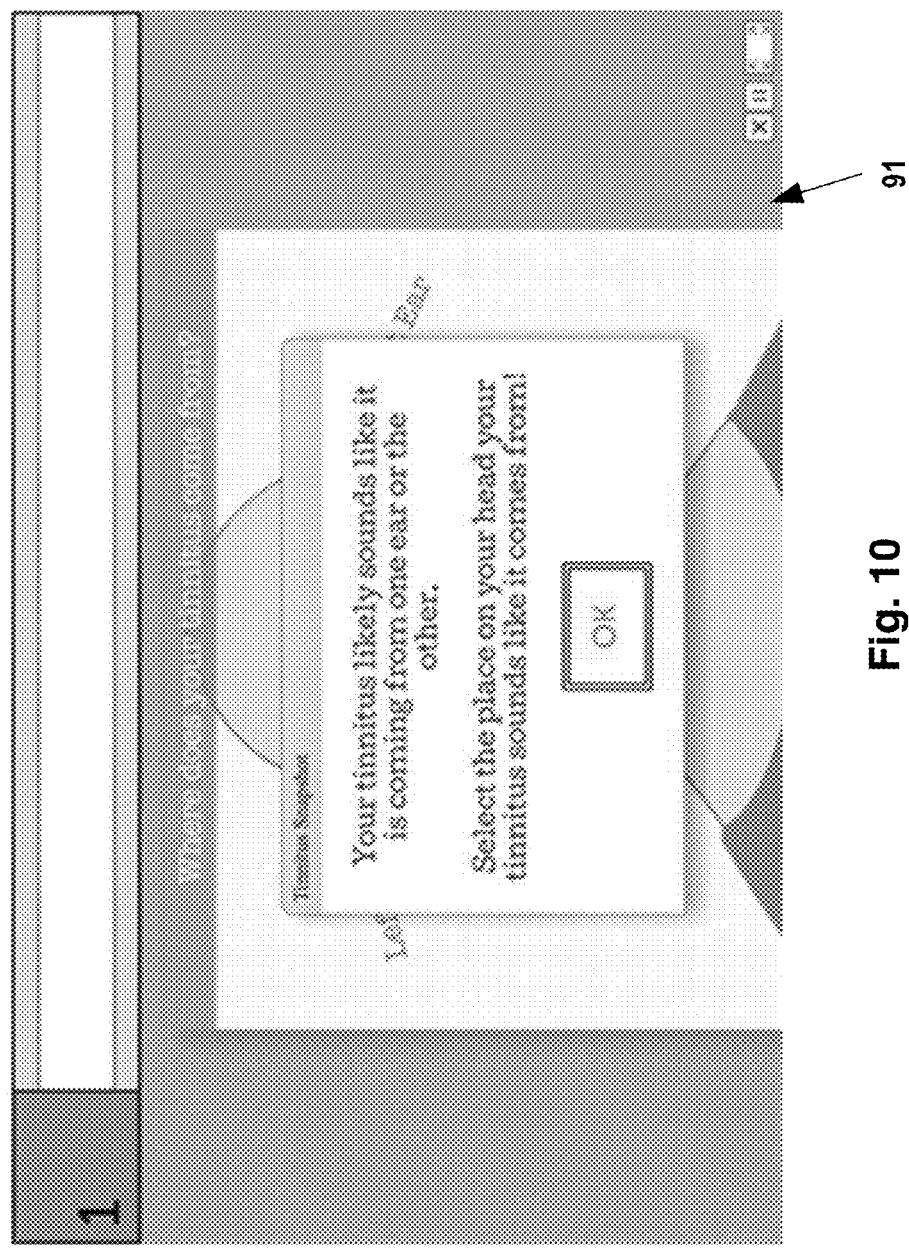
FIG. 10 illustrates another screenshot of the game illustrated in the previous figure.

FIGS. 6-10 illustrate screenshots 70, 75, 77, 89 and 91 of one embodiment of a tinnitus assessment. The assessment measures the extent to which tinnitus disrupts the participant's life. In FIG. 6, the assessment presents a questionnaire asking the participant to rate the impact of their tinnitus on their well-being. Questions are from the clinically-applied rating systems Tinnitus Handicap Inventory and Tinnitus Functional Index. In FIG. 7, the assessment encourages the participant to use headphones to help control sound quality and ensure the sounds are presented clearly and consistently. In FIG. 8, the assessment prompts the participant to select a sound that best matches the sound of their subjective tinnitus. The participant changes one or more sound parameters, such as frequency, by moving the cursor across an area on the screen, and then selecting when the closest matching sound is found. In FIG. 9, the assessment prompts the participant to indicate how well the sound they chose matches what their tinnitus actually sounds like. In FIG. 10, the assessment shows an image of a head and prompts the participant to select the place on the head where the tinnitus sounds like it comes from.

III. Interoaudioceptive Calibration Procedure

Most people have observed that the quality of one's own voice when speaking sounds different from one's voice replayed on from sound recording device. When a person perceives their own speech production as "sounding perfectly correct," they are referring to a more resonant, lowered pitch version of their voice received through the combination of conduction through the tissues of the head and conduction through the air.

A person perceives their own voice through two sources of stimulus—the external stimulus caused by the sound/pressure waves leaving one's mouth and reaching their ear, and the internal stimulus caused by vibrations translated through the neck and skull. While other people receive only this external stimulus, a person speaking receives both the internal and external stimulus.

This asymmetry is profoundly exemplified by many patients with aided hearing or speech. Such patients often describe the speech that they produce as "completely normal" and "completely understandable," even while they find the speech of others received by a cochlear implant or hearing aid to be completely or largely unintelligible.

We believe that this asymmetry can be leveraged to improve the degraded auditory processing abilities of a hearing-impaired individual. In particular, we believe that recovery or improvements in speech understanding can grow from the gradual neurological establishment of correspondences between the patient's own voice model and the voices of other speakers.

Figure 11:
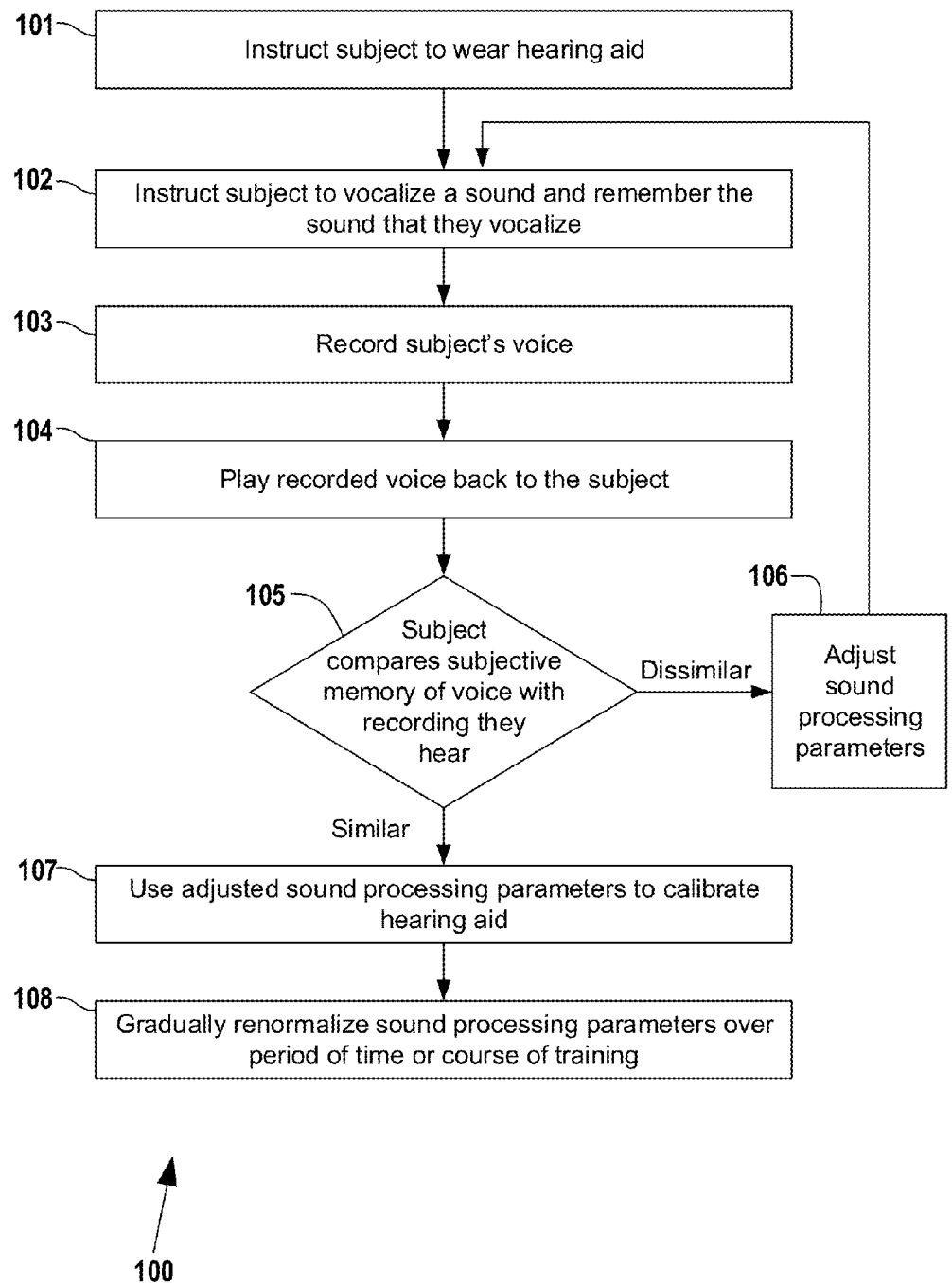
FIG. 11 is a functional block diagram of one embodiment of an interoaudioceptive calibration procedure for adjusting the sound processing parameters of a hearing aid or cochlear implant.
Figure 12:
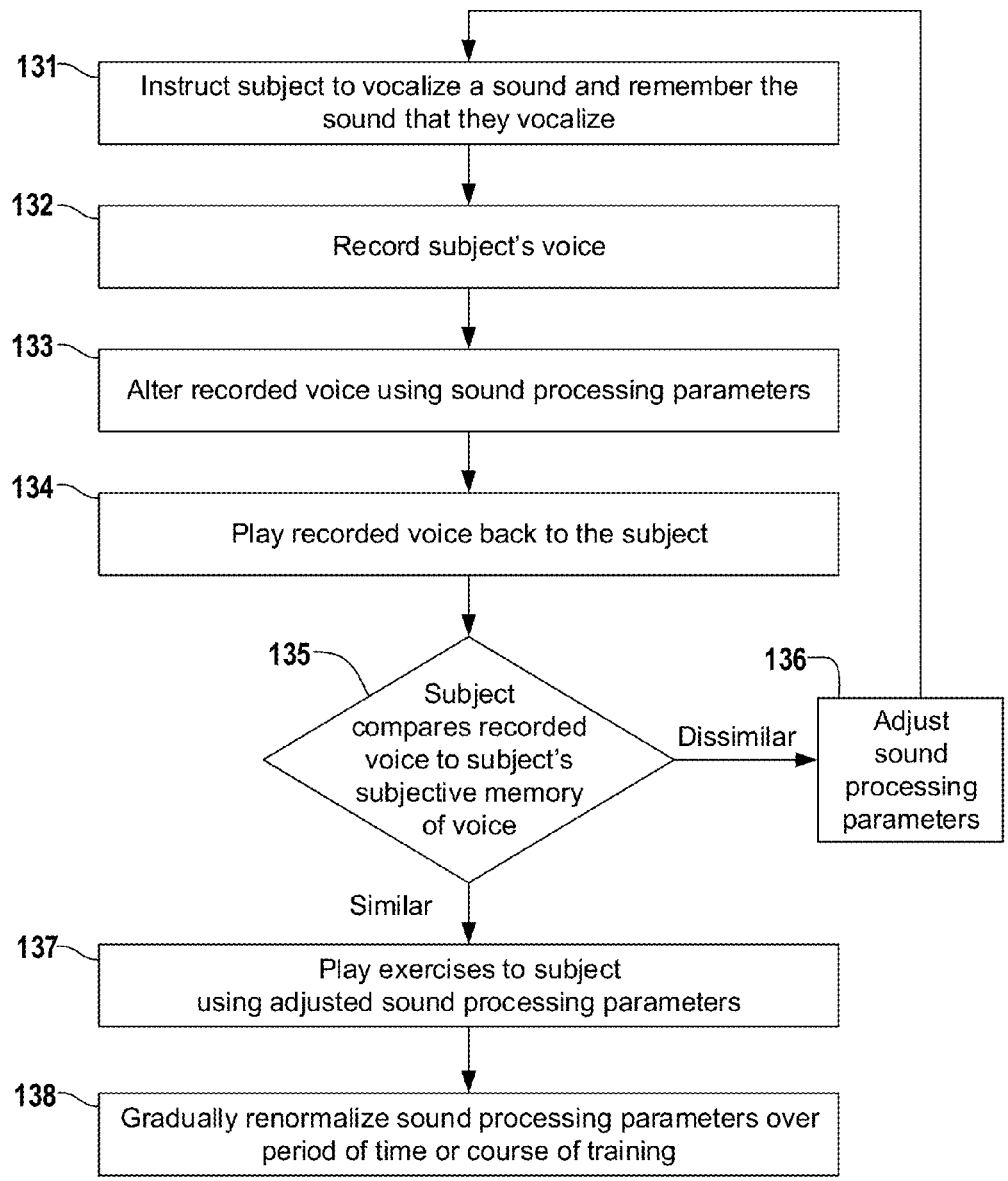
FIG. 12 is a functional block diagram of an embodiment of an interoaudioceptive calibration procedure used for improving the efficacy of auditory and cognitive training exercises.
Figure 13:
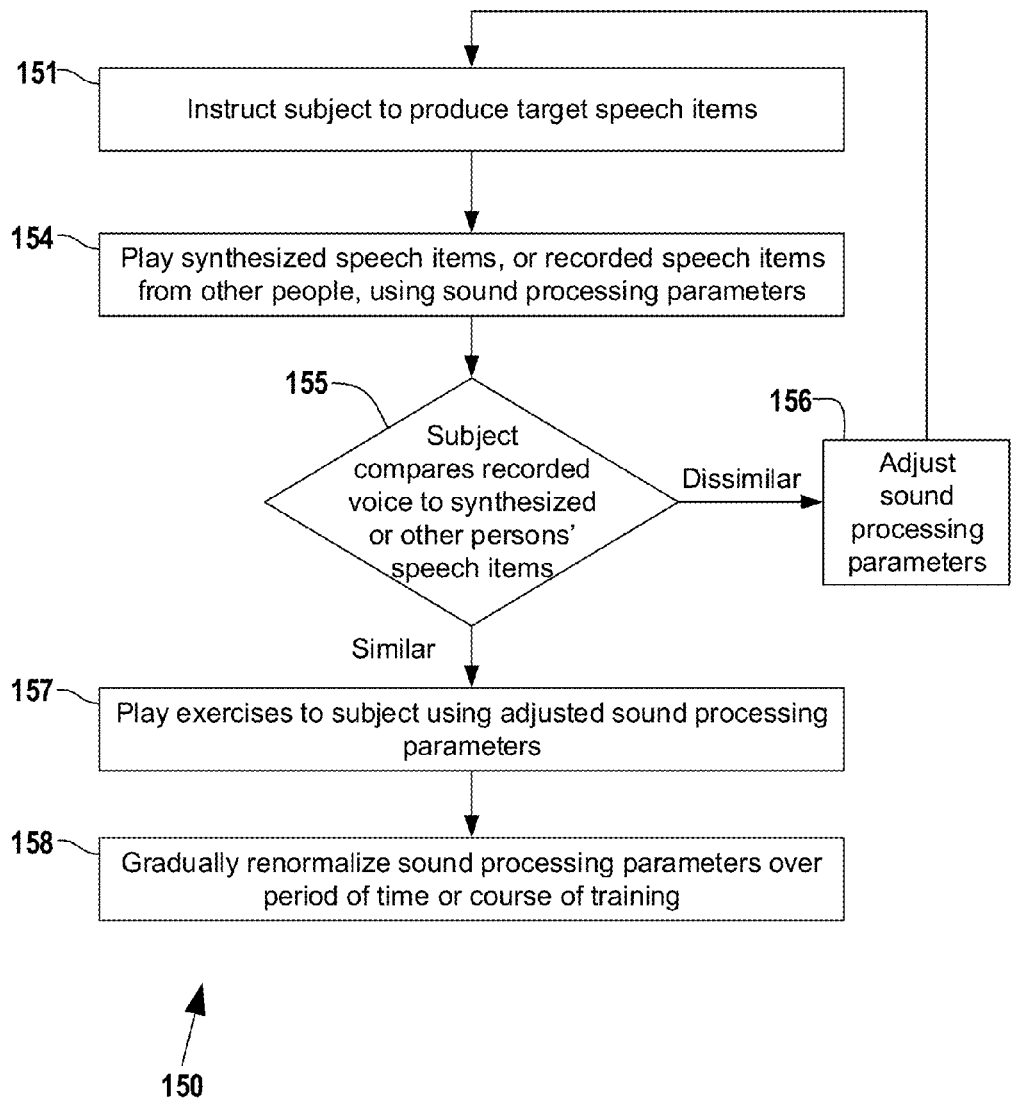
FIG. 13 is a functional block diagram of yet another embodiment of an interoaudioceptive calibration procedure.

FIGS. 11-13 illustrate three embodiments of interoauditoceptive calibration procedures and systems.

FIG. 11 illustrates an embodiment of an interoaudioceptive calibration procedure and system 100 for adjusting the sound processing parameters of a hearing aid or cochlear implant. In block 101, the system 100 instructs the subject, if possessing or being fitted with a hearing aid, to wear the hearing aid. This block can be skipped in the case of a user wearing a cochlear implant.

In block 102, the system 100 instructs the subject to vocalize a sound (such as a word or a tone) and remember the sound that they vocalize. In block 103, the system 100 records the subject's voice as they vocalize the designated sound. In block 104, the system 100 plays the recorded voice back to the subject.

In block 105, the system 100 queries the subject whether the recording they heard matches, or sounds similar to, their own memory of their voice. In an alternative embodiment, the system 100 queries the subject to identify which of two or more recordings sounds the best or best matches the user's memory of their voice. In yet another alternative embodiment, the system 100 queries the subject whether the pitch of the recording they heard sounds higher, lower, or approximately the same as the user's memory of their voice. The system 100 may also or alternatively query the subject whether the timbre, resonance, frequency at the high, middle, or low end of the spectrum, or other sound quality matches the user's memory of their voice.

If the subject indicates that the sounds are dissimilar (or a more optimal match), then flow proceeds to block 106. Otherwise, flow proceeds to block 107.

In block 106, the system 100 adjusts one or more sound processing parameters. In one embodiment, the sound processing parameters are the parameters used by the hearing aid or cochlear implant to process sound. In another embodiment, the sound processing parameters are parameters used to adjust the sound of the recorded voice as it is played back.

Based on the user's feedback, the system 100 identifies differences between the user's mixed intero- and exteroaudioception of their own voice and the user's exteroaudioception of their own voice. The system 100 effectively reduces these differences to a sound-processing algorithm, using a progressive matching strategy that alters a recorded speech replay of a patient's voice to match the qualities of one's own voice heard while speaking. The system 100 repeatedly plays recorded samples of the patient's voice, procures feedback from the patient regarding their comparisons of the recorded samples with the sound or sounds they remembered vocalizing, and adjusts the sound processing parameters until the patient indicates that they are satisfied that the recorded samples sound similar to what they remembered vocalizing, a threshold number of adjustments have been made, or an evaluation of the patient's feedback indicates a marginal benefit to further adjustments.

Then, in block 107, the program 100 uses the algorithm describing the altered speech to adjust the cochlear implant or hearing aid sound processing parameters to shape the hearing of all other voices to match the characteristics of the patient's voice received while speaking.

Finally, in step 108, the system 100 optionally gradually renormalizes the sound processing parameters over a period of time or course of training, reducing the distortion required to make hearing understandable and rendering a patient's hearing, with the aid of the hearing aid or cochlear implant, more realistic. In this manner, after the subject masters speech reception with this initial cochlear implant or hearing aid parameter setup, the distortions in speech used to match the speech of others with the self-received speech of the patient are progressively lessened in a series of automatic or audiologist or other clinician-implemented steps until, over a variable period of weeks or months, all speech is heard in its more variable, natural forms.

A more elaborate implementation of the interoauditoceptive calibration procedure and system 100 also instructs the patient to produce sound samples, and records the same, that exhibit functionally significant modulation characteristics such as pace, depth of modulation, rhythm, and other prosodic features. Moreover, as a subject masters his or her listening tasks, the algorithmic distortion related to that modulation characteristic (spectral and temporal and timbre and rhythm and in other ways prosodically matched voice) is progressively reduced in steps on the path of normal received speech.

FIG. 12 illustrates an embodiment of an interoauditoceptive calibration procedure and system 130 for improving the efficacy of auditory and cognitive training exercises. In block 131, the system 130 instructs the subject to vocalize a sound (such as a word or a tone) and remember the sound that they vocalize. In block 132, the system 130 records the subject's voice as they vocalize the designated sound. In block 133, the system 130 alters the recorded voice using sound processing parameters. In block 134, the system 130 plays the recorded voice, altered via the sound processing parameters, back to the subject.

In block 135, the system 130 queries the subject whether the recording they heard matches, or sounds similar to, their own memory of their voice. In an alternative embodiment, the system 130 queries the subject to identify which of two or more recordings sounds the best or best matches the user's memory of their voice. In yet another alternative embodiment, the system 130 queries the subject whether the pitch of the recording they heard sounds higher, lower, or approximately the same as the user's memory of their voice. The system 130 may also or alternatively query the subject whether the timbre, resonance, frequency at the high, middle, or low end of the spectrum, or other sound quality matches the user's memory of their voice.

If the subject indicates that the sounds are dissimilar (or a more optimal match), then flow proceeds to block 136. Otherwise, flow proceeds to block 137.

In block 136, the system 130 adjusts one or more sound processing parameters used, in step 133, to play the user's recorded voice. Flow proceeds back to step 131.

Based on the user's feedback, the system 130 identifies differences between the user's mixed intero- and exteroaudioception of their own voice and the user's exteroaudioception of their own voice. The system 130 effectively reduces these differences to a sound-processing algorithm, using a progressive matching strategy that alters a recorded speech replay of a patient's voice to match the qualities of one's own voice heard while speaking. Then, in block 137, the program 130 uses the algorithm describing the altered speech to select the auditory stimuli, and parameters (such as pitch and volume) of the auditory stimuli, played in auditory and cognitive training games and exercises.

Finally, in step 138, the system 130 optionally gradually renormalizes the sound processing parameters over a period of time or course of training, reducing the distortion required to make hearing understandable and rendering a patient's hearing more realistic.

A more elaborate implementation of the interoauditoceptive calibration procedure and system 130 also instructs the patient to produce sound samples, and records the same, that exhibit functionally significant modulation characteristics such as pace, depth of modulation, rhythm, and other prosodic features. Moreover, as a subject masters his or her listening tasks, the algorithmic distortion related to that modulation characteristic (spectral and temporal and timbre and rhythm and in other ways prosodically matched voice) is progressively reduced in steps on the path of normal received speech.

FIG. 13 illustrates yet another embodiment of an interoauditoceptive calibration procedure and system 150. In block 151, the system 150 instructs the subject to vocalize a sound (such as a word or a tone) and remember the sound that they vocalize. In block 154, the system 150 plays back one or more synthesized speech items, or recorded speech of other people, using one or more sound processing parameters. The speech items can, for example, be vowels or phonemic sounds, or syllables, words, phrases, or connected speech. Using initial speech items that are like the speaker's heard self-produced speech at the initial stage of training makes it easier for the subject to recognize the algorithmically produced voices of others.

In block 155, the system 150 queries the subject whether the synthesized speech recording or other-voice recording they heard matches, or sounds similar to, their own memory of their own voice. In an alternative embodiment, the system 150 queries the subject to identify which of two or more recordings sounds the best or best matches the user's memory of their voice. In yet another alternative embodiment, the system 150 queries the subject whether the pitch of the recording they heard sounds higher, lower, or approximately the same as the user's memory of their voice. The system 150 may also or alternatively query the subject whether the timbre, resonance, frequency at the high, middle, or low end of the spectrum, or other sound quality matches the user's memory of their voice.

If the subject indicates that the sounds are dissimilar (or a more optimal match), then flow proceeds to block 156. Otherwise, flow proceeds to block 157.

In block 156, the system 150 adjusts one or more sound processing parameters used, in step 154, to play the synthesized speech items or excerpts of other voices. Flow proceeds back to step 151.

Based on the user's feedback, the system 150 identifies differences between the user's mixed intero- and exteroaudioception of their own voice and the user's exteroaudioception of their own voice. The system 150 effectively reduces these differences to a sound-processing algorithm, using a progressive matching strategy that alters a recorded speech replay of a patient's voice to match the qualities of one's own voice heard while speaking. Then, in block 157, the program 150 uses the algorithm describing the altered speech to select the auditory stimuli, and parameters (such as pitch and volume) of the auditory stimuli, played in auditory and cognitive training games and exercises.

Finally, in step 158, the system 100 optionally gradually renormalizes the sound processing parameters over a period of time or course of training, reducing the distortion required to make hearing understandable and rendering a patient's hearing more realistic. Moreover, as a subject masters his or her listening tasks, the algorithmic distortion related to that modulation characteristic (spectral and temporal and timbre and rhythm and in other ways prosodically matched voice) is progressively reduced in steps on the path of normal received speech.

A more elaborate implementation of the interoaudioceptive calibration procedure and system 130 also instructs the patient to produce sound samples that exhibit functionally significant modulation characteristics such as pace, depth of modulation, rhythm, and other prosodic features. The system 130 also plays synthesized voice samples or actual voice samples from others that exhibit the same modulation characteristics, and challenges the subject whether they match.

In an important variation of this implementation, training extends to accurately receiving the voices of others heard at low volume (sound intensities), or against a background of environmental noises.

All of the aforementioned strategies accelerate the rate of acquisition of speech understanding or speech reception improvement in speech and hearing assisted patients.

To summarize, it will be seen that the interoaudioceptive calibration procedures and systems improve the user's speech recognition and general hearing by normalizing specific perceptual deficits that contribute to their hearing loss. The interoaudioceptive calibration procedures and systems may include regularly decoding the user's personal hearing profile to regulate an optimal training schedule that may be used with or without a hearing-aid.

Some embodiments of the training program 2 include an internet-based interoaudioceptive calibration system and procedure for improving hearing of hearing-impaired populations. The perceptual training consists of auditory discrimination exercises that improve the user's ability to judge low-level sound features such as timing, frequency and intensity, as well as high-level structures such as phonemes. The schedule involves training the user to initially discriminate exaggerated sounds and refining these distinctions to natural levels as they become able to make more sensitive distinctions. The incorporation of interoaudioceptive calibration procedures accelerates and improves the quality of the reacquisition of improvement in speech reception in an individual who has received a cochlear implant or hearing aid by leveraging the speech received from a user's voice as a guide for re-acquiring new or improved speech understanding.

Those skilled in the art should appreciate that they can readily use the disclosed conception and specific embodiments as a basis for designing or modifying other structures for carrying out the same purposes of the present invention without departing from the spirit and scope of the invention as defined by the appended claims. For example, various embodiments of the methods disclosed herein may be implemented by program instructions stored on a memory medium, or a plurality of memory media.

We claim:

1. An audiometry method comprising:
   providing a computer game environment for an audiometric exercise, the game environment displaying a plurality of visual stimuli that represent objects in a natural environment or video game theme, wherein each of a first subset of the visual stimuli are associated with an audio stimulus, and each of a second subset of the visual stimuli is not associated with an audio stimulus, and a means is provided of selecting any of the plurality of visual stimuli;
   wherein each audio stimulus comprises a fixed frequency tone associated with a fixed loudness level, and the loudness levels of each audio stimulus is separated from each other audio stimulus by discrete decibel increments; and
   performing the audiometric exercise by:
   (a) displaying the plurality of visual icons;
   (b) for each of at least two or more of the plurality of visual icons:
      receiving an initial selection of the visual icon to play audio stimulus associated with the visual icon;
      playing the audio stimulus, if any, associated with the visual icon; and
      if the user hears the audio stimulus associated with the visual icon, receiving the user's second selection of the visual icon to indicate that the user can hear the audio stimulus;
   (c) when a threshold loudness level is identifiable, identifying a threshold loudness level for the frequency tone of the audio stimuli and reducing a decibel increment between the loudness levels associated with the visual icons; and
   (d) when no threshold loudness level is identifiable because the user does not make any second selections, increasing the loudness levels associated with the plurality of visual icons.

2. The audiometry method of claim 1, further comprising challenging the user, in the computer game environment, to indicate as rapidly as possible whether they can hear the frequency tones, and providing sensory feedback on an accuracy and speed of the user's response.

3. The audiometry method of claim 2, further comprising:
   displaying to the user, in the computer game environment, a plurality of visual objects, each associated with one of the tones; and
   challenging the user to hover a pointer over the objects to play the tones and to select the objects if they are able to hear the tones.

4. The audiometry method of claim 1, further comprising:
   selecting stimuli to use in a subsequent game that are a function of results obtained from the audiometry exercise.

5. The audiometry method of claim 4, wherein the subsequent game is an auditory perceptual training game, and the game stimuli comprise auditory signals.

6. The audiometry method of claim 1, further comprising for each frequency tone:
   identifying a minimum-amplitude threshold for the frequency tone as the quietest loudness level that the user indicated that they could hear;

subsequent to identifying the minimum-amplitude threshold, playing the frequency tone at a plurality of loudness levels distributed around the minimum-amplitude threshold; and repeating the preceding two steps until the user repeatedly selects loudness levels for the frequency tone that are within a threshold of each other.

7. The audiometry method of claim 6, wherein the plurality of loudness levels at which the frequency tone is played are uniformly distributed across discrete decibel increments.

8. The audiometry method of claim 7, further comprising:
after determining a minimum-amplitude threshold from a first distribution of loudness levels, playing the frequency tone at a second distribution of loudness levels having smaller discrete decibel increments.

9. The audiometry method of claim 5, wherein for each frequency tone, if the user does not indicate hearing at any of a first plurality of loudness levels, playing the frequency tone again at a second plurality of loudness levels that are distributed about a mean loudness level that is louder than a mean loudness level of the first plurality of loudness levels.

10. The audiometry method of claim 5, further comprising:
after identifying a consistent minimum-amplitude threshold for a first frequency, playing a tone at another frequency multiple times at a plurality of loudness levels until a consistent minimum-amplitude threshold is identified; and repeating the preceding steps until a consistent minimum-amplitude threshold is identified for each frequency in the distribution of frequencies, wherein consistent means within a threshold error range.

11. The audiometry method of claim 1, wherein the means of selecting any of the plurality of stimuli comprises a keyboard, mouse, trackpad, touch screen, microphone, camera, or other sensor.

* * * * *